United States Patent
Wang et al.

(10) Patent No.: US 12,169,164 B2
(45) Date of Patent: Dec. 17, 2024

(54) DIFFUSIVE GRADIENTS IN THIN FILMS (DGT) TEST DEVICE FOR LAKE WATER AND TEST METHOD USING SAME

(71) Applicant: CHINESE RESEARCH ACADEMY OF ENVIRONMENTAL SCIENCES, Beijing (CN)

(72) Inventors: Shuhang Wang, Beijing (CN); Zhihao Wu, Beijing (CN); Xia Jiang, Beijing (CN); Bo Zhang, Beijing (CN); Kun Wang, Beijing (CN); Wenwen Wang, Beijing (CN); Junyi Chen, Beijing (CN); Li Zhao, Beijing (CN); Qing Cai, Beijing (CN); Cheng Yao, Beijing (CN)

(73) Assignee: CHINESE RESEARCH ACADEMY OF ENVIRONMENTAL SCIENCES, Beijing (CN)

( * ) Notice: Subject to any disclaimer, the term of this patent is extended or adjusted under 35 U.S.C. 154(b) by 653 days.

(21) Appl. No.: 17/142,495

(22) Filed: Jan. 6, 2021

(65) Prior Publication Data
US 2021/0208033 A1 Jul. 8, 2021

(30) Foreign Application Priority Data
Jan. 7, 2020 (CN) .......................... 202010012861.7

(51) Int. Cl.
*G01N 1/14* (2006.01)
*G01N 33/18* (2006.01)

(52) U.S. Cl.
CPC ........... *G01N 1/14* (2013.01); *G01N 33/1826* (2013.01)

(58) Field of Classification Search
CPC ............ G01N 1/12; G01N 33/18; G01N 1/10; G01N 2001/2071; G01N 1/14; G01N 1/16; G01N 33/1826
(Continued)

(56) References Cited

U.S. PATENT DOCUMENTS 5,739,439 A * 4/1998 Gruidel .................... G01N 1/26
73/863.31

FOREIGN PATENT DOCUMENTS

CN 105255728 A * 1/2016
CN 109238775 A * 1/2019 ............. A01K 63/00
(Continued)

OTHER PUBLICATIONS

Murphy, J. et al. "A Modified Single Solution Method for the Determination of Phosphate in Natural Waters," Analytica Chimica Acta, 27, pp. 31-36, 1962.
(Continued)

*Primary Examiner* — Daniel S Larkin
*Assistant Examiner* — Nashmiya S Fayyaz
(74) *Attorney, Agent, or Firm* — Tutunjian & Bitetto, P.C.

(57) ABSTRACT

A diffusive gradients in thin films (DGT) test device for lake water, including: a floating ball and a plurality of water sampling units. A DGT detection device, a water quality detection device with a multi-parameter probe, and a water sampling device are disposed in each of the water sampling units. The water sampling device includes: a plurality of sampling bottles, each of the sampling bottles is provided with an inlet pipe and an exhaust pipe, each of the inlet pipes and exhaust pipes is provided with a one-way solenoid valve; a peristaltic pump, a water sample outlet of the peristaltic pump communicates with the inlet pipes of the plurality of sampling bottles via a multi-way connector; the exhaust pipes of the plurality of sampling bottles are con-
(Continued)

nected to an exhaust manifold via a multi-way connector; a control device connected with the peristaltic pump and each of the one-way solenoid valves.

18 Claims, 5 Drawing Sheets

(58) Field of Classification Search
USPC .............. 73/864.34, 864.51, 864.63, 864.67
See application file for complete search history.

(56) References Cited

FOREIGN PATENT DOCUMENTS

| CN | 211374206 U | * | 8/2020 |
| CN | 115326491 A | * | 11/2022 |

OTHER PUBLICATIONS

Zhang, H. et al. "In situ high resolution measurements of fluxes of Ni, Cu, Fe, and Mn and concentrations of Zn and Cd in porewaters by DGT," Geochimica et Cosmochimica Acta, vol. 59, No. 20, pp. 4181-4192, 1995.
"Water quality—Determination of nitrate-nitrogen—Ultravioletspectrophotometry," HJ/T 346-2007 put in effect as of May 1, 2007, Ministry of Ecology and Environment, The People's Republic of China, http://english.mee.gov.cn/standards_reports/standards/water_environment/method_standard2/200807/t20080704_125017.htm, accessed Jan. 5, 2021.
"Water quality—Determination of ammonia nitrogen—Nessler's reagent spectrophotometry," HJ 535-2009 replacing GB 7479-87 and put in effect as of Apr. 1, 2010, Ministry of Ecology and Environment, The People's Republic of China, http://english.mee.gov.cn/standards_reports/standards/water_environment/method_standard2/201010/ 20101027_196755.htm accessed Jan. 5, 2021.

* cited by examiner

DIFFUSIVE GRADIENTS IN THIN FILMS (DGT) TEST DEVICE FOR LAKE WATER AND TEST METHOD USING SAME

This application claims priority to Chinese Patent Application No. 202010012861.7 filed Jan. 7, 2020 and entitled "DIFFUSIVE GRADIENTS IN THIN FILMS (DGT) TEST DEVICE FOR LAKE WATER AND TEST METHOD USING SAME," the entire disclosure of which is incorporated herein by this reference.

TECHNICAL FIELD

The present disclosure belongs to the research field of lake water eutrophication mechanism and diffusive gradients in thin films (DGT) technique, and specifically relates to a DGT test device for lake water and a test method using the same.

BACKGROUND

The diffusive gradients in thin films (DGT) technique can be used to monitor the labile metals/nutrient salts/oxyanions in water/sediments/soil. The principle is as follows: DGT measures the amount of a solute that diffuses through a diffusive gel and a membrane filter where a concentration gradient forms; and after passing through the diffusive layer of DOT device, the solute is quickly bonded by a binding gel behind the diffusive gel, which continuously removes solutes and maintains the concentration gradient during operation (Zhang et al., 1995). Based on Fick's first law, the time-averaged flux (F) of DGT and the time-averaged concentration ($C_{DGT}$) at the DGT/solution interface can be calculated.

In the prior art, DGT piston can usually be used to determine the eutrophic elements (nitrogen/phosphorus) in lake water, thereby revealing the bioavailability of the eutrophic elements in the water. At present, there are two types of DOT test methods for lake water: a first type: lake water samples are collected using sampling bottles, and then the ex-situ DOT test DOT ex-situ test is conducted for the water samples in a laboratory; and a second type: DGT piston is mounted on a test device, the test device is placed in lake water, and in situ test is conducted in the surface water or water overlying sediment in the lake.

However, the first type of method mentioned above has the following problems: the collected water samples, when detected in the laboratory, the physicochemical properties such as Eh, pH, temperature and conductivity for water samples have been changed, which affect the chemical reaction in the water and the form of the elements; thus these reasons mentioned above lead to the distortion of the form, composition and bioavailability of elements in the collected water samples. Therefore, the ex-situ DGT piston test in a laboratory cannot accurately reflect the form and bioavailability of elements and the physicochemical properties of water on site.

The second type of method is to achieve in-situ test of DOT piston test in water bodies by some simple devices. The devices used in the prior art includes the following: (1) a simple device obtained by mounting DGT in a PVC pipe, which is put into surface water to achieve DGT test; (2) a device obtained by fixing DOT to a crutch-shaped structure, where, DGT piston is disposed on the upper end of the device, and the lower end is inserted into sediment and fixed to achieve the test of water overlying sediment; and (3) a spindle or flat device equipped with DGT piston test inside, which is used for the test of water overlying a sediment.

The above mentioned test devices can achieve the DGT test in surface water or overlying water of a lake, but have the following shortcomings: (1) The devices cannot accurately collect water samples in the area for DGT test a DGT test area simultaneously, but can only collect water samples near the test zone at the beginning or end of the test. This kind of water sampling method has a low sampling frequency, so that the analysis result of a water sample cannot be compared with the time-integrated concentration of DGT, that is, the bioavailability of elements in water and the degree of eutrophication of water cannot be accurately studied by comparing the time-averaged concentration of DGT with test results of various water samples collected at different time point; (2) the existing devices cannot simultaneously measure the physicochemical properties of the area for DOT test, which can only test the physicochemical properties of the surface water using a hand-held water quality analyzer before or at the end of DGT test, but cannot in-situ measure the physicochemical properties (Eh, pH, DO, salinity, temperature, etc.) of the intermediate water and water overlying a sediment. The time-averaged concentration of DGT combined with the physicochemical properties of water samples is an important method to study the eutrophication mechanism of water at different depths.

It is a challenge for inventing a novel device for DGT test in water, which can (1) achieve in-situ DGT test for surface water, the intermediate water and the water overlying sediment; (2) synchronously collect water samples from the area for DGT test and determine the physicochemical properties thereof at the three water layers; and (3) synchronously obtain DGT concentrations of nitrogen and phosphorus in lake water profile; and (4) obtain the nitrogen and phosphorus concentrations and physicochemical properties of water at a plurality of time nodes by conventional analysis methods. Based on the test and measurement mentioned above, the research results can reflect the eutrophication mechanism of lake water at different depths. It is also the problem for the development of the device for "in-situ" DGT test in water.

SUMMARY

The present disclosure solves the technical problem that the DOT test devices in the present technical field cannot realize in-situ DGT test for water at a plurality of depths, cannot synchronously (1) collect water samples from DGT test zones; and (2) determine the physicochemical properties of water. This invention provides a DGT test device that can simultaneously (i) achieve in-situ DGT test of the surface water, the intermediate water and the water overlying a sediment (ii) obtain DGT concentrations of nitrogen and phosphorus in lake water profile, the element concentrations and the physicochemical properties of water by the conventional analysis method, and (iii) collect samples. The present disclosure also provides a test method based on DOT test device.

To solve the above technical problem, the present disclosure provides the following technical solution.

The present disclosure provides a DGT test device for lake water, including: a floating ball; and a plurality of water sampling units arranged below the floating ball in sequence along a vertical direction in water. Every two adjacent water sampling units are connected with each other via a rope, and the topmost water sampling unit is also connected with the floating ball via a rope. Each water sampling unit is equipped with a DGT detection device, a water quality detection device with multi-parameter probe, and a water sampling device, equipped in. The water sampling device includes: a plurality of sampling bottles, where, each of the sampling bottle is provided with an inlet pipe and an exhaust pipe, and each of the inlet pipe and exhaust pipe is provided with a one-way solenoid valve: a peristaltic pump, where, a water sample outlet of the peristaltic pump is connected with the inlet pipes of the plurality of sampling bottles via a first multi-way connector, and the exhaust pipes of the plurality of sampling bottles are connected to an exhaust manifold via a second multi-way connector; and a control device connected with the peristaltic pump and the one-way solenoid valve on each of the inlet pipes and exhaust pipes.

The water sampling device may be provided with an integrated sampler, including: a fixing plate, where, a power supply and a control device are fixed on the bottom surface of the fixing plate; a fixing base for water pump located below the fixing plate and fixedly connected to the fixing plate, where, the peristaltic pump is mounted on the water pump fixing base; a solenoid valve and connector fixing ring located below the water pump fixing base and fixedly connected to the water pump fixing base, where, a socket is mounted on the solenoid valve and connector fixing ring, and the first multi-way connector, the second multi-way connector and the one-way solenoid valve are mounted on the socket; and a sampling bottle fixing ring located below the solenoid valve fixing ring and fixedly connected to the solenoid valve fixing ring, where, a sampling bottle is mounted below the sampling bottle fixing ring. The power supply is connected with the peristaltic pump, the one-way solenoid valve and the control device via wires, separately. DOT detection device is provided with a DGT fixing ring, a plurality of placement holes are evenly arranged along a circumferential direction of the DGT fixing ring, and a plurality of DGT pistons can be respectively mounted in the plurality of placement holes.

The water quality detection device with a multi-parameter probe includes a base provided with a mounting hole, and a detection electrode is fixedly mounted in the mounting hole of the base through an electrode fixing cover. A fixing rod may be fixedly mounted below the base, and the base of the water quality detection device with a multi-parameter probe may be fixedly mounted above the DGT detection device through the fixing rod. A probe at the bottom of the detection electrode may run through the DGT fixing ring of the DGT test device and extend below the DGT fixing ring.

The integrated sampler may be further provided with a data memory, and the data memory is fixedly mounted on the fixing plate and connected to the detection electrode.

Four sampling bottles may be provided; both the first and second multi-way connectors may be a five-way connector; and three water sampling units may be provided.

A sealing cylinder may be further provided, the integrated sampler may be removably mounted inside the sealing cylinder, and the DGT fixing ring of the DGT detection device may be sleeved on the outer wall of the sealing cylinder and located on an upper part of the sealing cylinder.

The exhaust manifold and a suction pipe of the peristaltic pump may both run through the DGT detection device and the water quality detection device with a multi-parameter probe and finally reach the base of the water quality detection device with multi-parameter probe; and an exhaust outlet of the exhaust manifold and a water sample inlet of the suction pipe may both be disposed on an upper surface of the base.

A sampler auxiliary frame may be further provided, and the water sampling units may be removably mounted on the sampler auxiliary frame in an appropriate manner.

The present disclosure provides a test method based on the DOT test device for lake water, including: (1) placing the DGT test device in lake water; (2) using the DGT detection devices in the water sampling units at different depths to conduct DOT detection in water at a corresponding depth, and using the water quality detection device with a multi-parameter probe to detect water quality indicators; opening the one-way solenoid valves on the inlet pipe and the exhaust pipe of the sampling bottle of the water sampling device, and using the control device to control actions of the peristaltic pump and the one-way solenoid valves on the inlet pipe and the exhaust pipe so that water is pumped into the sampling bottle at regular intervals for sampling; and (3) retrieving the DGT test device from the lake water, and taking out water samples in the sampling bottles and DGT pistons for processing and analysis.

The DGT test device for lake water in the present disclosure has the following advantages: The device described in the present disclosure can not only ensure the in-situ test for DGT piston at three water depths in lake water, but also simultaneously collect water samples at the three water depths and measure the physicochemical properties (Eh, pH, temperature, and conductivity) thereof, thus the measurement by this device truly reflects the bioavailability of nitrogen, phosphorus, or metal elements in the water. The device is equipped with a plurality of separate test units that can detect water at different depths, so as to realize the task of testing water at a plurality of depths, which is suitable for the study of distribution characteristics of eutrophic elements at a plurality of water depths in a deep lake profile. The device is suitable for the study of eutrophic element (nitrogen/phosphorus) distribution characteristics and eutrophication mechanism in lake water profile.

A plurality of sampling bottles are disposed in the DGT test device for lake water described in the present implementation. The water sampling device is provided with a first multi-way connector, one opening of the first multi-way connector is a liquid inlet that is connected with the water sample outlet of the peristaltic pump, and the remaining openings of the first multi-way connector are liquid outlets that respectively communicate with the inlet pipes of the plurality of sampling bottles. The exhaust pipes of the sampling bottles are connected to the exhaust manifold via a second multi-way connector. A solenoid valve is disposed on each of the exhaust pipes and the inlet pipes. The water sampling device is provided with a control device that is used to periodically control actions of the peristaltic pump and the solenoid valves so that a plurality of water samples can be collected during one day.

In order to make the technical solutions of the DGT test device for lake water and the test method provided in the present disclosure more comprehensible, the present disclosure will be further described in detail below in conjunction with specific drawings and embodiments.

Figure 1:
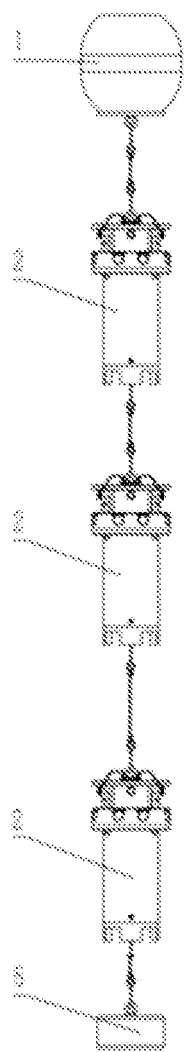
FIG. 1 is a schematic diagram of the overall structure of the DGT test device for lake water according to the present disclosure.

Reference numerals in the drawings are as follows:

1: floating ball; 2: water sampling unit; 4: sampler auxiliary frame: 5: counterweight chassis;

21: integrated sampler; 22: DGT detection device; 23: the quality detection device with a multi-parameter probe;

221: DGT piston; 222: guide post; 223: DGT fixing ring; 224: electrode fixing base; 225: BPK6 plunger; 227: placement hole;

231: electrode wire; 232: multi-parameter water quality electrode; 233: electrode fixing cover; 234: base; 235: water sample inlet; 236: top suspension ring; 237: exhaust outlet; 238: sealing connector: 239: third O-ring seal; 2310: fixing rod; 2311: electrode fixing sleeve;

212: fixing plate; 213: exhaust manifold; 214: first O-ring seal; 215: data memory; 216: suction pipe of peristaltic pump; 217: start switch; 218: power supply fixing side plate; 219: switch mounting base; 2110: PLC controller; 2111: power supply; 2112: power supply fixing block; 2113: first multi-way connector; 2114: water pump fixing base; 2115: peristaltic pump; 2116: socket; 2117: solenoid valve and connector fixing ring; 2118: one-way solenoid valve; 2119: sampling bottle fixing ring; 2120: sampling bottle assembly fixing block; 2121: circuit board mounting sleeve: 2122: solenoid valve module fixing ring: 2123: sampling bottle fixing base; 2124: sampling bottle; 2125: rotating screw; 2126: sealing cylinder; 2127: second O-ring seal; 2128: sealing bottom cover; 2129: bottom suspension ring; 2130: second multi-way connector; 2131: power supply holder; 2132: mounting ring at the top of the sealing bottom cover; 2133: inlet pipe; 2134: exhaust pipe; and 41: hole on a placement ring of the sampler auxiliary frame.

DETAILED DESCRIPTION

The implementation provides a DGT test device for lake water, which is made of opaque PVC plastics, foamed plastics, integrated circuits (ICs), wires, ordinary plastics, stainless steel, and the like. As shown in FIG. 1, there is a floating ball 1 with a diameter of 30 cm at the top of the device. The floating ball 1 is made of a foamed plastic and undergoes some buoyancy in water, which allows the device to suspend in water and can be used for location. Three water sampling units 2 are arranged in sequence along a vertical direction from top to bottom below the floating ball 1, which are respectively used to detect the water quality of the surface water, intermediate water and lower water and realize the DGT test. A counterweight chassis 5 is disposed at the bottom of the bottommost water sampling unit 2. Every two adjacent water sampling units 2 are connected with each other via a cable, and the topmost water sampling unit 2 is also connected with the floating ball 1 via a cable. In this implementation, each water sampling unit 2 has a height of 51.9 cm and a maximum outer diameter of 23 cm; and the counterweight chassis 5 has a diameter of 15 cm, a thickness of 8 cm, and a weight of 3 kg, which is hoisted below the third layer of water sampling unit 2. When in use, the counterweight chassis 5 is placed on surface sediment, and the depths of the three layers of water sampling units 2 in water are determined by the lake water depth and the cables connecting the three units 2.

Figure 2:
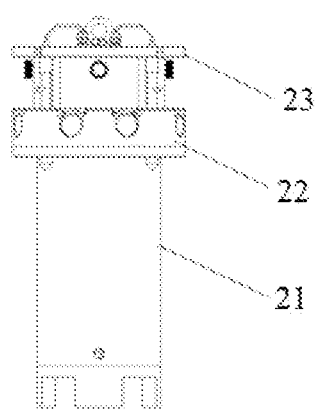
FIG. 2 is a schematic diagram of the overall structure of the water sampling unit of the DGT test device for lake water according to the present disclosure.
Figure 3:
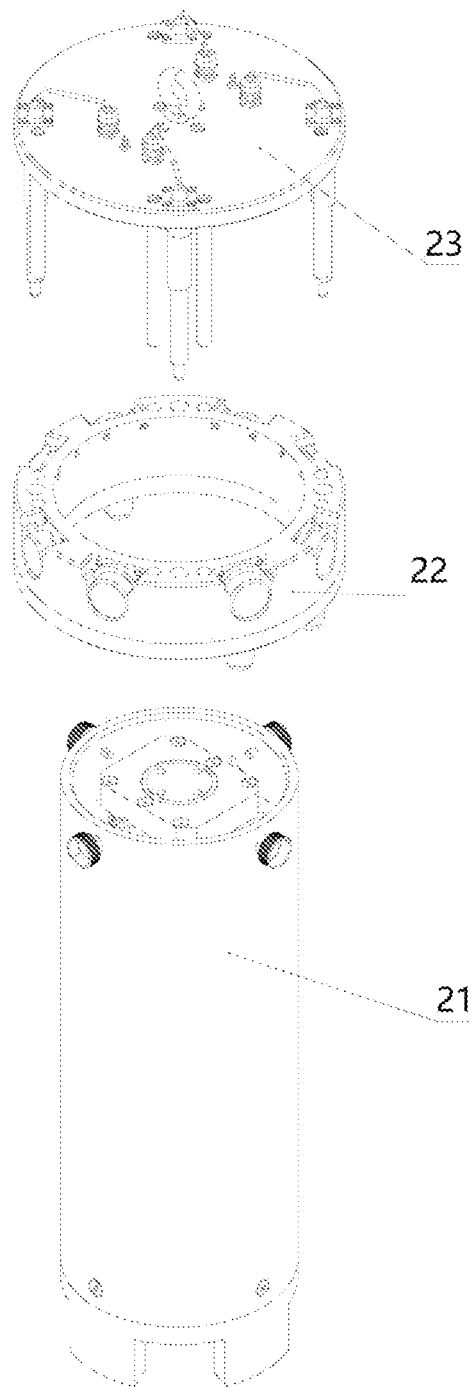
FIG. 3 is an exploded view of the water sampling unit according to the present disclosure.
Figure 5:
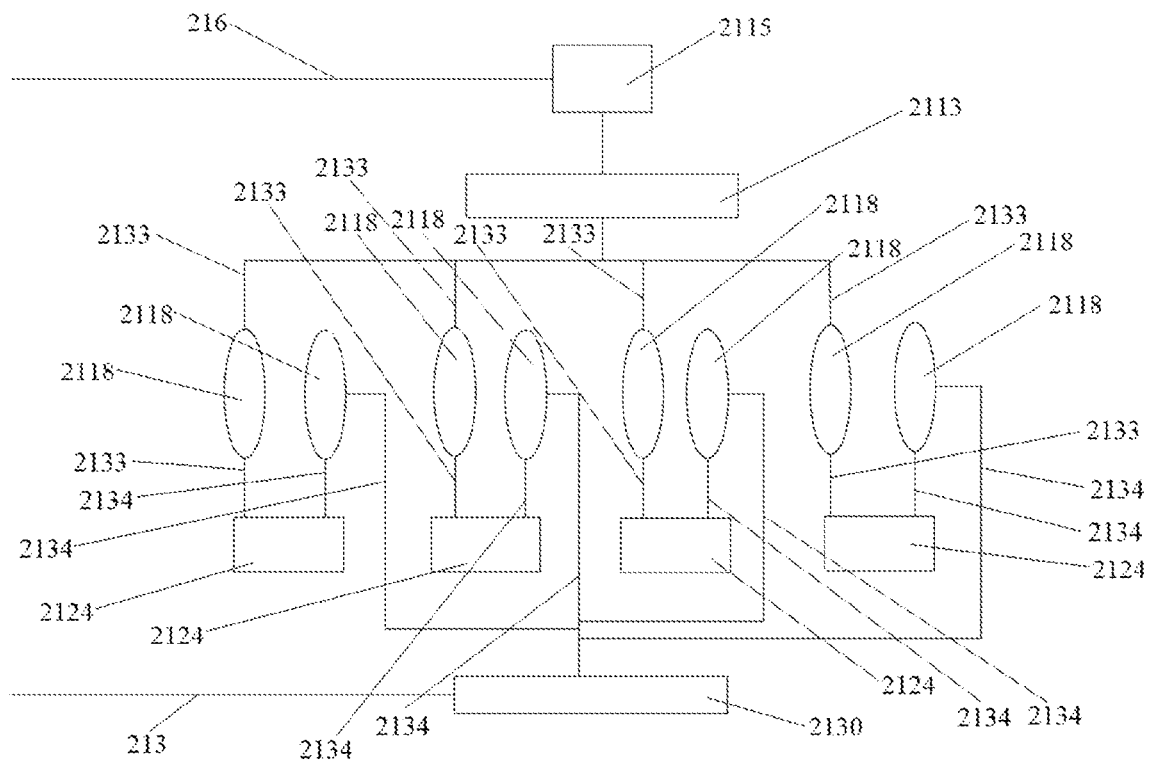
FIG. 5 is a schematic diagram illustrating the connection relationships among the multi-way connector, the one-way solenoid valve, and the peristaltic pump of the integrated sampler according to the present disclosure.

As shown in FIG. 2 and FIG. 3, a DGT detection device 22, a water quality detection device with a multi-parameter probe 23, and a water sampling device are disposed in each of the water sampling units 2. The water sampling device includes: a plurality of sampling bottles 2124, where, each of the sampling bottles 2124 is provided with an inlet pipe 2133 and an exhaust pipe 2134, and each of the inlet pipes 2133 and exhaust pipes 2134 is provided with a one-way solenoid valve 2118; a peristaltic pump 2115, where, a water sample outlet of the peristaltic pump 2115 is connected to the inlet pipes 2133 of the plurality of sampling bottles 2124 via a first multi-way connector 2113, and the exhaust pipes 2134 of the plurality of sampling bottles 2124 are connected to an exhaust manifold 213 via a second multi-way connector 2130; and a control device connected to the peristaltic pump 2115 and the one-way solenoid valve 2118 on each of the inlet pipes 2133 and exhaust pipes 2134. In this implementation, four sampling bottles 2124 are provided, and both the first multi-way connector 2113 and the second multi-way connector 2130 are a five-way connector. One opening of the first multi-way connector 2113 is connected to the water sample outlet of the peristaltic pump 2115, and the other four openings respectively connected to the inlet pipes 2133 of the four sampling bottles 2124. One opening of the second multi-way connector 2130 is connected to the exhaust manifold 213, and the other four openings respectively connected to the exhaust pipes 2134 of the four sampling bottles 2124. The connection relationships among the multi-way connector, the one-way solenoid valve, and the peristaltic pump are shown in FIG. 5.

Figure 4:
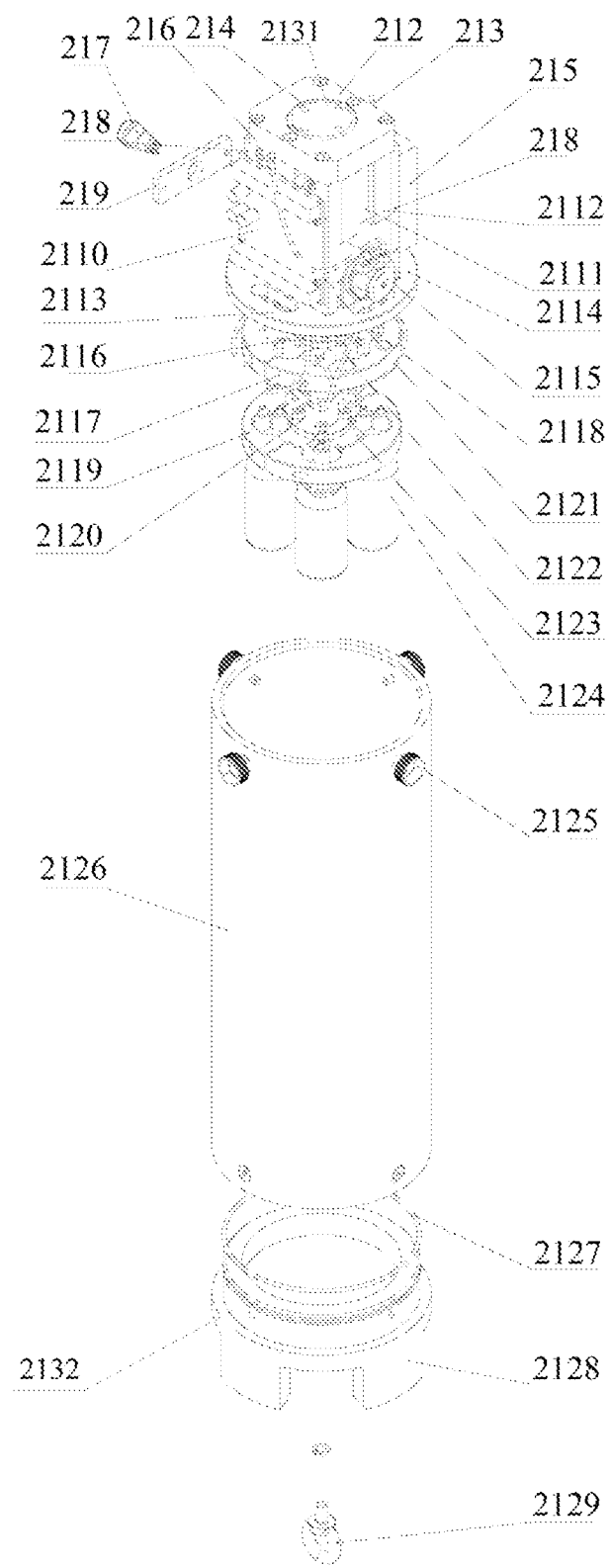
FIG. 4 is an exploded view of the integrated sampler according to the present disclosure.

The water sampling device in this implementation is provided with an integrated sampler 21. As shown in FIG. 4, the integrated sampler 21 includes:

a fixing plate 212, where, a power supply 2111, a control device, and a data memory 215 are fixedly mounted on a bottom surface of the fixing plate 212; the control device is a PLC controller 2110; a central position of the fixing plate 212 is provided with a mounting hole, and the mounting hole of the fixing plate 212 is provided with a disc-shaped power supply holder 2131; the power supply holder is removably mounted on the fixing plate 212, and specifically fixed to the fixing plate 212 by screws; a first O-ring seal 214 is disposed at a junction of the power supply holder 2131 with the mounting hole of the fixing plate 212; the power supply 2111 is fixedly mounted on the power supply holder 2131 through power supply fixing side plates 218; the power supply fixing side plates 218 are located on both sides of the power supply 2111; a power supply fixing block 2112 is also disposed between each of the power supply fixing side plates 218 and the power supply

2111; a circuit board of the PLC controller 2110 is arranged along the vertical direction, and is fixed on an outer wall of the power supply fixing side plate 218 through a circuit board mounting sleeve 2121; the power supply 2111 is also provided with a start switch 217 fixedly mounted on the fixing plate 212 through a switch mounting base 219; and the power supply 2111 is connected to the control device 2110 and the data memory 215;

a water pump fixing base 2114 located below the fixing plate 212 and fixedly connected to the fixing plate 212, where, the water pump fixing base 2114 is fixedly connected to the power supply fixing side plates 218 through bolts; the peristaltic pump 2115 is mounted on an upper surface of the water pump fixing base 2114; the peristaltic pump 2115 is connected to the power supply 2111;

a solenoid valve and connector fixing ring 2117 fixedly mounted below the water pump fixing base 2114, where, the solenoid valve and connector fixing ring 2117 is fixedly connected to the water pump fixing base 2114 through a cylindrical fastening located at a central position: the solenoid valve and connector fixing ring 2117 is located below the water pump fixing base 2114 and fixedly connected to the water pump fixing base 2114; a socket 2116 is mounted on the solenoid valve and connector fixing ring 2117, and the first multi-way connector 2113, the second multi-way connector 2130, and the one-way solenoid valves 2118 on the inlet pipes 2133 and exhaust pipes 2134 are fixedly mounted on the socket 2116; the plurality of solenoid valves 2118 are fixedly connected through a solenoid valve module fixing ring 2122; and the one-way solenoid valves 2118 are connected to the power supply 2111;

a sampling bottle fixing ring 2119 located below the solenoid valve and connector fixing ring 2117, where, the sampling bottle fixing ring 2119 is fixedly connected to the solenoid valve and connector fixing ring 2117 also through a cylindrical fastening located at the central position; a sampling bottle assembly fixing block 2120 is formed at the bottom of the cylindrical fastening; a disc-shaped sampling bottle fixing base 2123 is provided at the central position of the sampling bottle fixing ring 2119; the sampling bottle fixing base 2123 is fixedly connected to the sampling bottle assembly fixing block 2120 through bolts; and four sampling bottles 2124 are mounted below the sampling bottle fixing base 2123.

Figure 6:
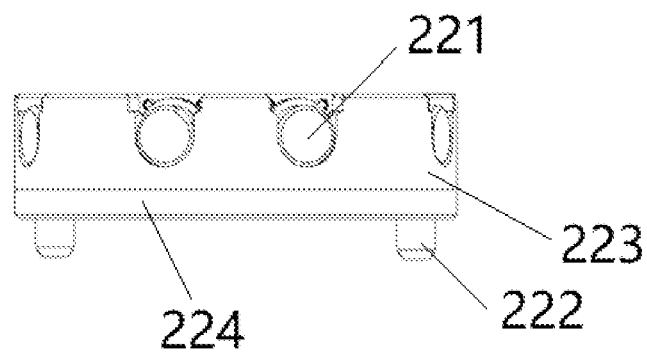
FIG. 6 is a schematic diagram of the overall structure of the DGT detection device according to the present disclosure.
Figure 7:
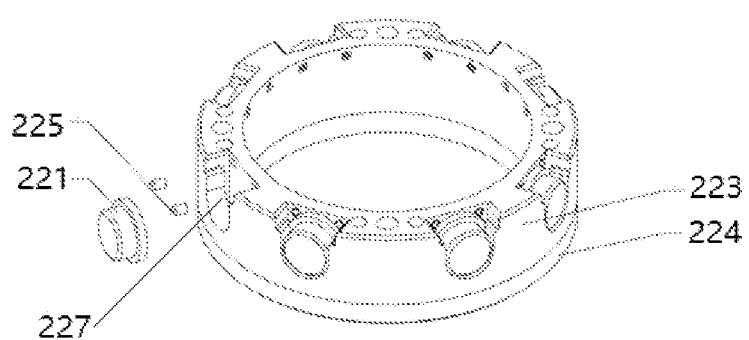
FIG. 7 is a partially exploded view of the structure of the DOT detection device according to the present disclosure.

A DOT detection device 22 is also disposed above the integrated sampler 21. As shown in FIG. 6 and FIG. 7, the DGT detection device 22 includes a DGT fixing ring 223. In this implementation, 8 placement holes 227 are disposed on the DGT fixing ring 223, and the 8 placement holes 227 are arranged in a row and are evenly arranged along a circumferential direction of the DGT fixing ring 223, so that 8 DGT pistons 221 can be mounted. As an alternative implementation, the DGT placement holes 227 of the DGT detection device 22 can also be arranged in a double-layer mounting manner, so that the number of DGT pistons can be increased to 16. In this implementation, the DGT fixing ring 223 has an outer diameter of 23 cm and a height of 6.5 cm. The placement hole 227 is a circular recess, and two BPK6 plungers 225 are mounted on the upper part inside the recess to fix the DGT piston 221 in the recess. The plungers 225 can be automatically released when the DGT is removed.

Figure 8:
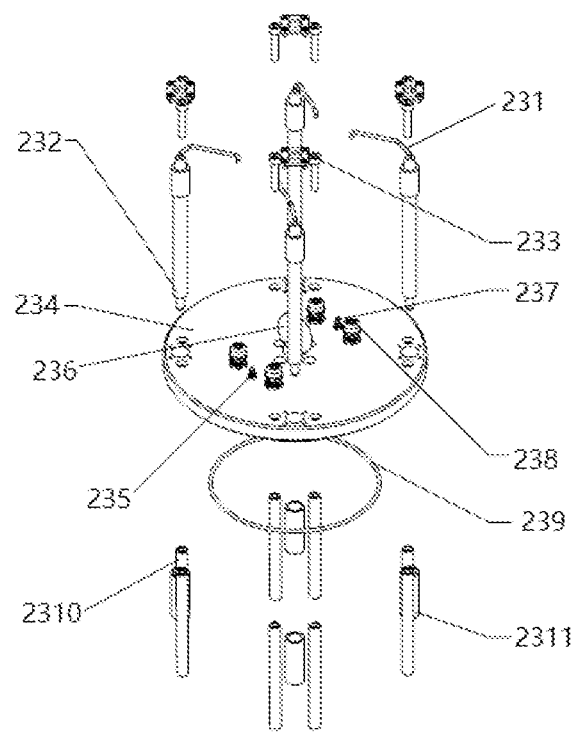
FIG. 8 is an exploded view of water the quality detection device with a multi-parameter probe according to the present disclosure.

The water quality detection device with a multi-parameter probe 23 is shown in FIG. 8 and includes four multi-parameter water quality electrodes 232 that can be used to determine Eh, pH, temperature, and conductivity, respectively. The four multi-parameter water quality electrodes 232 are respectively mounted vertically between a base 234 and the electrode fixing base 224 located below the DGT fixing ring 223, and the base 234 is fixedly mounted above the DGT detection device 22 through a fixing rod 2310. In this implementation, a lower end of the fixing rod 2310 runs through the DGT fixing ring 223 and is fixed on the electrode fixing base 224 through bolts. A terminal wire 231 of the multi-parameter water quality electrode 232 passes through a sealing connector 238 and then through a cavity below the base 234, and connected to the power supply 2111 and the data memory 215. The data memory 215 is fixedly mounted on the fixing plate 212 of the integrated sampler 21 and is arranged close to the power supply fixing side plate 218. A probe of the multi-parameter water quality electrode 232 passes through the electrode fixing sleeve 2311 between two fixing rods 2310 and then through the DGT fixing ring 223 and the electrode fixing base 224 below the DGT fixing ring 223, and finally extends to a position 2 cm below the DGT detection device 22. The top of the electrode fixing sleeve 2311 is in contact with the base 234, and the bottom is in contact with the DGT fixing ring 223. In this implementation, the detection electrode is fixedly mounted on the base 234 through the electrode fixing cover 233, the base 234 is provided with mounting holes, and two fixing bolts are disposed on a lower surface of the electrode fixing cover 233. The electrode fixing cover 233 covers the top of the electrode, and the fixing bolts can be inserted into the mounting holes on the base 234 to realize the fixing of the top of the electrode.

In this implementation, the water sampling unit 2 is also provided with a sealing cylinder 2126, and the integrated sampler 21 is removably mounted in the sealing cylinder 2126; a removable sealing bottom cover 2128 is disposed at the bottom of the sealing cylinder 2126; a mounting ring 2132 is disposed at the top of the sealing bottom cover 2128, and the mounting ring 2132 is suitable for inserting into a bottom opening of the sealing cylinder 2126 and is fixed on the sealing cylinder 2126 through screws; a base is disposed at a lower end of the mounting ring 2132, and a step is formed at a junction of the base with the mounting ring 2132; when the mounting ring is inserted into the bottom opening of the sealing cylinder 2126, the step is in contact with the bottom of the sealing cylinder 2126 to achieve a better sealing effect; and a second O-ring seal 2127 is disposed between the step and a bottom edge of the sealing cylinder 2126. A bottom suspension ring 2129 is disposed on a bottom surface of the sealing bottom cover 2128 to connect with the water sampling unit 2 or the counterweight chassis 5 located there below.

In this implementation, the sealing cylinder 2126 has a diameter of 19.7 cm and a height of 48.5 cm. In this implementation, the sealing cylinder 2126 is a cylinder, and a cylindrical holder is disposed on a bottom surface of the base 234; the top of the sealing cylinder 2126 is open, and the top opening of the sealing cylinder 2126 can be sleeved on the cylindrical holder and fixedly mounted on the holder through a rotating screw 2125; when the sealing cylinder 2126 is mounted on the holder, the top edge of the sealing cylinder 2126 conflicts with a bottom surface of the base 234; and a third O-ring seal 239 is disposed between the top of the sealing cylinder 2126 and the base 234. A top suspension ring 236 is disposed at the top of the base 234 to connect with the floating ball 1 or the water sampling unit 2 there above.

After the water quality detection device with a multi-parameter probe 23 and the sealing cylinder 2126 are fixedly mounted, the DOT fixing ring 223 is sleeved on an outer wall of the sealing cylinder 2126 and is located on an upper part of the sealing cylinder 2126.

In this implementation, the exhaust manifold 213 and the suction pipe 216 of the peristaltic pump 2115 both run through the DGT detection device 22 and the water quality detection device with a multi-parameter probe 23, and finally reach the base 234 of the water quality detection device with a multi-parameter probe 23, and the exhaust outlet 237 of the exhaust manifold 213 and the water sample inlet 235 of the suction pipe 216 are all disposed on an upper surface of the base.

Figure 9:
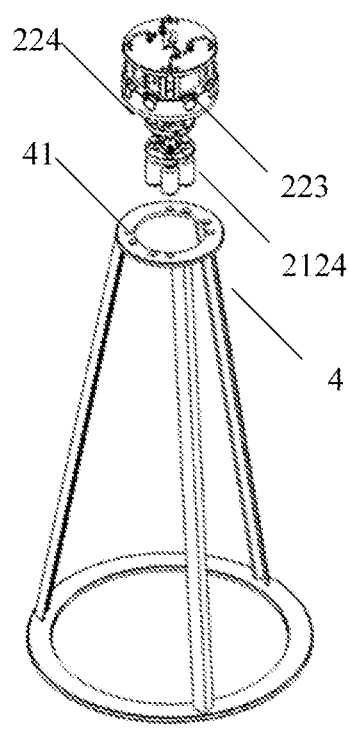
FIG. 9 is a schematic diagram illustrating the mounting of the water sampling unit on the sampler auxiliary frame after the sealing cylinder is removed according to the present disclosure.

The DGT test device for lake water is also provided with a sampler auxiliary frame 4. As shown in FIG. 9, a placement ring is disposed on the top of the sampler auxiliary frame, and a plurality of holes 41 are disposed on the placement ring; a plurality of guide posts 222 are disposed on a bottom surface of the electrode fixing base 224; and the plurality of guide posts 222 are arranged corresponding to the plurality of holes on the placement ring and are suitable for mounting in the holes of the placement ring. After the experiment ends, the sealing cylinder can be removed, and the parts other than the sealing cylinder in the integrated sampler 21 that are still in a fixed connection state, the DGT detection device 22 and the water quality detection device with a multi-parameter probe 23 can be placed on the sampler auxiliary frame, which facilitates the disassembly of the device.

The lake water experiment method described in this embodiment includes the following steps:
(1) Selection of study areas: the study areas were selected in Lake Dianchi, Yunnan province (China), with a water depth of 4 m to 10 m; and a total of 5 sampling sites were selected.
(2) Preparation of DOT experimental materials: all DGT devices for this experiment were purchased from Nanjing Weishen Environmental Protection Technology Co., Ltd. (China). The DGT piston device included: ZrO, A520 E and CMI-7000 binding gels, which were used to test phosphorus ($PO_i^{3-}$), nitrate ($NO_3N$) and ammonium ($NH_4$—N) in water, respectively; a diffusive gel, which was a 0.50 mm agarose diffusive gel; a membrane filter, which was a polyethersulfone microporous membrane filter with a pore size of 0.13 mm; a DGT piston shell, with a sampling area of 3.14 $cm^2$; and the gel layer with a diameter of 2.5 cm. The above DGT materials were assembled to form three DGT pistons for measuring phosphorus, $NO_3$—N and $NH_4$—N. The DOT pistons were sorted and placed into plastic bags, 2 mL of a 0.001 M NaCl solution was dropped in plastic bags, and then DGT pistons were stored in a refrigerator at 4° C. Before the field test, the DGT was mounted on a DGT settlement device, and the test device was immediately placed in water.
(3) Placement of DGT test devices for lake water: The depth of lake water was determined by a portable ultrasonic water depth sensor, and the water depths for five sampling sites were 4.2, 4.8 m, 5.7 m, 7.8, and 5.2 in, respectively. The surface water depth refers to 10 cm below the water layer; the intermediate water depths include 2.1, 2.4, 2.85, 3.9, and 2.6 m; and the water overlying a sediment refers to water at depths of 4.0, 4.6, 5.5, 7.6, and 5.0 m. Cables were used to connect the top floating ball 1, three vertically-distributed water sampling units 2, and the counterweight chassis 5 in series. The counterweight chassis 5, the three water sampling units 2, and the top floating ball 1 were sequentially placed in water; and when each water sampling unit 2 was placed in water, the start switch 217 was pressed to start the multi-parameter electrode and sampling-related devices in the integrated sampler 21.
(4) Taking out of the DGT test devices for lake water: 24 h later, three DGT test devices for water were retrieved according to the position of the top floating ball 1; when the test device was taken out, the start switch 217 was immediately turned off, and DOT pistons were taken out from the recess of the DGT placement hole 227, rinsed with deionized water, and put in a plastic bag; a few drops of the 0.001 M NaCl solution was dropped, and DOT pistons were stored; at the same time, the electrode, sampling bottle and data memory 215 were taken out, and components in the DOT test device for water were removed; and the above DGT pistons and sampling bottles were brought back to a laboratory, and immediately used for determination or stored in a refrigerator at 4° C. The data memory 215 was brought back to the laboratory, and data were acquired and analyzed using computer software. Moreover, all parts in the device were overhauled. Through processing of the computer software, the physicochemical properties of the three layers of water at the five sampling sites were obtained, namely, Eh, pH, temperature, and conductivity.
(5) The subsequent processing and analysis of DGT: the window of DOT piston was opened, and the membrane filter, diffusive gel and binding gel were taken out. Then, the ZrO binding gel (for phosphorus determination) was eluted with 1.0 mol $L^{-1}$ NaOH for 24 h, and then neutralized with 1.0 mol $L^{-1}$ $H_2SO_4$; and molybdenum blue spectrophotometry (ascorbic acid reduction) (Murphy and Riley, 1962) was used to determine the phosphorus concentration of the neutralized elution solution. A520E ($NO_3$—N determination) and CMT-7000 ($Ni_4$—N determination) binding gels were eluted with 2 mol $L^{-1}$ NaCl; and then ultraviolet spectrophotometry (dual wavelength) (HJ-T 346-2007) and Nessler's reagent colorimetric method (HJ 535-2009) were used to determine $NO_3$—N and $NH_4$—N concentrations of two elution solutions, respectively. According to the above method, DGT concentrations of phosphorus, $NO_3$—N and $NH_4$—N in the three layers of water at the five sampling sites were obtained.
(6) The subsequent treatment and analysis of water samples: The water samples collected in the sampling bottles were tested for nitrogen and phosphorus forms. The molybdenum blue spectrophotometry (ascorbic acid reduction) (Murphy and Riley, 1962) was used to determine: total phosphorus (TP), dissolved total phosphorus (DTP), and soluble reactive phosphorus (SRP); and the ultraviolet spectrophotometry (dual wavelength) (HT 346-2007) and Nessler's reagent colorimetric method (H-J 535-2009) were used to determine: $NO_3$—N(nitrate nitrogen), $NH_4$—N(ammonium nitrogen), and TN (total nitrogen). According to the above method, the TP, DTP, SRP, $NO_3$—N, $NH_4$—N and TN concentrations in water samples at the five sampling sites were determined.
(7) The subsequent research: According to the DGT concentrations of nitrogen and phosphorus in the three layers of water at the five sampling sites, various forms and concentrations of nitrogen and phosphorus and the physicochemical properties of water determined by a conventional analysis method, and the hydrological, watershed and geographic background of Lake Dianchi, the degree of eutrophication and the eutrophication mechanism of nitrogen and phosphorus in water profiles at the five sampling sites were studied.

The abovementioned embodiments are merely illustrative of several implementations of the present disclosure, and the description thereof is more specific and detailed, but should not be construed as limiting the patent scope of the present disclosure. It should be noted that those of ordinary skill in the art can further make several variations and improvements without departing from the idea of the present disclosure, but such variations and improvements shall all fall within the protection scope of the present disclosure. Therefore, the protection scope of the present disclosure shall be subject to the protection scope defined by the claims.

What is claimed is:

1. A diffusive gradients in thin films (DGT) test device for lake water, comprising:
   a floating ball; and
   a plurality of water sampling units arranged below the floating ball in sequence along a vertical direction, wherein, every two adjacent water sampling units are connected to each other via a rope, and the topmost water sampling unit is connected to the floating ball also via a rope;
   a DGT detection device, a water quality detection device with a multi-parameter probe, and a water sampling device are disposed in each of the water sampling units; and
   each water sampling device comprises:
      a plurality of sampling bottles, wherein, each of the sampling bottles is provided with an inlet pipe and an exhaust pipe; and each of the inlet pipes and exhaust pipes is provided with a one-way solenoid valve;
      a peristaltic pump, wherein, a water sample outlet of the peristaltic pump connected to the inlet pipes of the plurality of sampling bottles via a first multi-way connector; and the exhaust pipes of the plurality of sampling bottles are connected to an exhaust manifold via a second multi-way connector; and
      a control device connected to the peristaltic pump and the one-way solenoid valve on each of the inlet pipes and exhaust pipes.

2. The DGT test device for lake water according to claim 1, wherein, each said water sampling device is provided with an integrated sampler comprising:
   a fixing plate, wherein, a power supply and the control device are fixedly mounted on a bottom surface of the fixing plate;
   a water pump fixing base located below the fixing plate and fixedly connected to the fixing plate, wherein, the peristaltic pump is mounted on the water pump fixing base;
   a solenoid valve and connector fixing ring located below the water pump fixing base and fixedly connected to the water pump fixing base, wherein, a socket is mounted on the solenoid valve and connector fixing ring, and the first multi-way connector, the second multi-way connector and the one-way solenoid valve on each of the inlet on each of the inlet pipes and exhaust pipes are mounted on the socket; and
   a sampling bottle fixing ring located below the solenoid valve and connector fixing ring and fixedly connected to the solenoid valve and connector fixing ring, wherein, a corresponding one of the plurality of sampling bottles is mounted below the sampling bottle fixing ring;
   wherein, the power supply is connected to the peristaltic pump, the one-way solenoid valves and the control device via wires, separately.

3. The DGT test device for lake water according to claim 2, wherein, each DGT detection device is provided with a DGT fixing ring, a plurality of placement holes are evenly arranged along a circumferential direction of the DGT fixing ring, and a plurality of DGT probes are respectively mounted in the plurality of placement holes.

4. The DGT test device for lake water according to claim 3, wherein, each water quality detection device with a multi-parameter probe comprises a base provided with a mounting hole, wherein a detection electrode is fixedly mounted in the mounting hole of the base through an electrode fixing cover, wherein a fixing rod is fixedly mounted below the base, and the base of each water quality detection device with a multi-parameter probe is fixedly mounted above each DGT detection device through the fixing rod, and wherein a probe at the bottom of the detection electrode runs through and extends below the DGT fixing ring of each DGT detection device.

5. The DGT test device for lake water according to claim 4, wherein, each said integrated sampler is further provided with a data memory, and the data memory is fixedly mounted on the fixing plate of each said integrated sampler and connected to the detection electrode mounted in the mounting hole of the base of each water quality detection device with a multi-parameter probe.

6. The DGT test device for lake water according to claim 5, wherein, the plurality of sampling bottles comprises four sampling bottles; both the first multi-way connector and the second multi-way connector are a five-way connector; and three water sampling units are provided.

7. The DGT test device for lake water according to claim 6, wherein, a sealing cylinder is further provided, each said integrated sampler is removably mounted inside the sealing cylinder, and the DGT fixing ring of each DGT detection device is sleeved on an outer wall of the sealing cylinder and located on an upper part of the sealing cylinder.

8. The DGT test device for lake water according to claim 7, wherein, the exhaust manifold and a suction pipe of the peristaltic pump both run through each DGT detection device and each water quality detection device with a multi-parameter probe and finally reach the base of each water quality detection device with a multi-parameter probe; and an exhaust outlet of the exhaust manifold and a water sample inlet of the suction pipe are both disposed on an upper surface of the base of each water quality detection device with a multi-parameter probe.

9. The DGT test device for lake water according to claim 8, wherein, a sampler auxiliary frame is further provided, and the water sampling units are removably mounted on the sampler auxiliary frame in an appropriate manner.

10. A test method based on the DGT test device for lake water according to claim 1, wherein each DGT detection device is provided with DGT pistons mounted in placement holes disposed on the DGT detection device, the test method comprising: (1) placing the DGT test device for lake water in lake water; (2) using the DGT detection devices in the water sampling units at different depths to conduct DGT detection on water at a corresponding depth, and using each water quality detection device with a multi-parameter probe to detect water quality; opening the one-way solenoid valve on the inlet pipe and the one-way solenoid valve on the exhaust pipe of each of the sampling bottles of each water sampling device, and using the control device to control actions of the peristaltic pump, the one-way solenoid valve on the inlet pipe and the one-way solenoid valve on the exhaust pipe so that water is pumped into the sampling bottles of each water sampling device at regular intervals for sampling; and (3) retrieving DGT test device for lake water from the lake, and taking out water samples in the DGT pistons and the sampling bottles for processing and analysis.

11. A test method based on the DGT test device for lake water according to claim 2, wherein each DOT detection device is provided with DGT pistons mounted in placement holes disclosed on the DGT detection device, the test method comprising: (1) placing the DGT test device for lake water in lake water; (2) using the DGT detection devices in the water sampling units at different depths to conduct DGT detection on water at a corresponding depth, and using each water quality detection device with a multi-parameter probe to detect water quality; opening the one-way solenoid valve on the inlet pipe and the one-way solenoid valve on the exhaust pipe of each of the sampling bottles of each water sampling device, and using the control device to control actions of the peristaltic pump, the one-way solenoid valve on the inlet pipe and the one-way solenoid valve on the exhaust pipe so that water is pumped into the sampling bottles of each water sampling device at regular intervals for sampling; and (3) retrieving DGT test device for lake water from the lake, and taking out water samples in the DGT pistons and the sampling bottles for processing and analysis.

12. A test method based on the DGT test device for lake water according to claim 3, wherein each DGT detection device is provided with DGT pistons mounted in placement holes disposed on the DGT detection device, the test method comprising: (1) placing the DGT test device for lake water in lake water; (2) using the DGT detection devices in the water sampling units at different depths to conduct DGT detection on water at a corresponding depth, and using each water quality detection device with a multi-parameter probe to detect water quality; opening the one-way solenoid valve on the inlet pipe and the one-way solenoid valve on the exhaust pipe of each of the sampling bottles of each water sampling device, and using the control device to control actions of the peristaltic pump, the one-way solenoid valve on the inlet pipe and the one-way solenoid valve on the exhaust pipe so that water is pumped into the sampling bottles of each water sampling device at regular intervals for sampling; and (3) retrieving DGT test device for lake water from the lake, and taking out water samples in the DGT pistons and the sampling bottles for processing and analysis.

13. A test method based on the DGT test device for lake water according to claim 4, wherein each DGT detection device is provided with DGT pistons mounted in placement holes disposed on the DGT detection device, the test method comprising: (1) placing the DGT test device for lake water in lake water; (2) using the DGT detection devices in the water sampling units at different depths to conduct DGT detection on water at a corresponding depth, and using each water quality detection device with a multi-parameter probe to detect water quality; opening the one-way solenoid valve on the inlet pipe and the one-way solenoid valve on the exhaust pipe of each of the sampling bottles of each water sampling device, and using the control device to control actions of the peristaltic pump, the one-way solenoid valve on the inlet pipe and the one-way solenoid valve on the exhaust pipe so that water is pumped into the sampling bottles of each water sampling device at regular intervals for sampling; and (3) retrieving DGT test device for lake water from the lake, and taking out water samples in the DGT pistons and the sampling bottles for processing and analysis.

14. A test method based on the DGT test device for lake water according to claim 5, wherein each DGT detection device is provided with DGT pistons mounted in placement holes disposed on the DGT detection device, the test method comprising: (1) placing the DGT test device for lake water in lake water; (2) using the DGT detection devices in the water sampling units at different depths to conduct DGT detection on water at a corresponding depth, and using each water quality detection device with a multi-parameter probe to detect water quality; opening the one-way solenoid valve on the inlet pipe and the one-way solenoid valve on the exhaust pipe of each of the sampling bottles of each water sampling device, and using the control device to control actions of the peristaltic pump, the one-way solenoid valve on the inlet pipe and the one-way solenoid valve on the exhaust pipe so that water is pumped into the sampling bottles of each water sampling device at regular intervals for sampling; and (3) retrieving DGT test device for lake water from the lake, and taking out water samples in the DGT pistons and the sampling bottles for processing and analysis.

15. A test method based on the DGT test device for lake water according to claim 6, wherein each DGT detection device is provided with DGT pistons mounted in placement holes disposed on the DGT detection device, the test method comprising: (1) placing the DGT test device for lake water in lake water; (2) using the DGT detection devices in the water sampling units at different depths to conduct DGT detection on water at a corresponding depth, and using each water quality detection device with a multi-parameter probe to detect water quality; opening the one-way solenoid valve on the inlet pipe and the one-way solenoid valve on the exhaust pipe of each of the sampling bottles of each water sampling device, and using the control device to control actions of the peristaltic pump, the one-way solenoid valve on the inlet pipe and the one-way solenoid valve on the exhaust pipe so that water is pumped into the sampling bottles of each water sampling device at regular intervals for sampling; and (3) retrieving DGT test device for lake water from the lake, and taking out water samples in the DGT pistons and the sampling bottles for processing and analysis.

16. A test method based on the DGT test device for lake water according to claim 7, wherein each DGT detection device is provided with DGT pistons mounted in placement holes disposed on the DGT detection device, the test method comprising: (1) placing the DGT test device for lake water in lake water; (2) using the DGT detection devices in the water sampling units at different depths to conduct DGT detection on water at a corresponding depth, and using each water quality detection device with a multi-parameter probe to detect water quality; opening the one-way solenoid valve on the inlet pipe and the one-way solenoid valve on the exhaust pipe of each of the sampling bottles of each water sampling device, and using the control device to control actions of the peristaltic pump, the one-way solenoid valve on the inlet pipe and the one-way solenoid valve on the exhaust pipe so that water is pumped into the sampling bottles of each water sampling device at regular intervals for sampling; and (3) retrieving DGT test device for lake water from the lake, and taking out water samples in the DGT pistons and the sampling bottles for processing and analysis.

17. A test method based on the DGT test device for lake water according to claim 8, wherein each DGT detection device is provided with DGT pistons mounted in placement holes disposed on the DGT detection device, the test method comprising: (1) placing the DGT test device for lake water in lake water; (2) using the DGT detection devices in the water sampling units at different depths to conduct DGT detection on water at a corresponding depth, and using each water quality detection device with a multi-parameter probe to detect water quality; opening the one-way solenoid valve on the inlet pipe and the one-way solenoid valve on the exhaust pipe of each of the sampling bottles of each water sampling device, and using the control device to control actions of the peristaltic pump, the one-way solenoid valve on the inlet pipe and the one-way solenoid valve on the exhaust pipe so that water is pumped into the sampling bottles of each water sampling device at regular intervals for sampling; and (3) retrieving DGT test device for lake water from the lake, and taking out water samples in the DGT pistons and the sampling bottles for processing and analysis.

18. A test method based on the DGT test device for lake water according to claim 9, wherein each DGT detection device is provided with DGT pistons mounted in placement holes disposed on the DGT detection device, the test method comprising: (1) placing the DGT test device for lake water in lake water; (2) using the DGT detection devices in the water sampling units at different depths to conduct DGT detection on water at a corresponding depth, and using each water quality detection device with a multi-parameter probe to detect water quality; opening the one-way solenoid valve on the inlet pipe and the one-way solenoid valve on the exhaust pipe of each of the sampling bottles of each water sampling device, and using the control device to control actions of the peristaltic pump, the one-way solenoid valve on the inlet pipe and the one-way solenoid valve on the exhaust pipe so that water is pumped into the sampling bottles of each water sampling device at regular intervals for sampling; and (3) retrieving DGT test device for lake water from the lake, and taking out water samples in the DGT pistons and the sampling bottles for processing and analysis.

\* \* \* \* \*